United States Patent [19]

Jackman et al.

[11] Patent Number: 4,943,660
[45] Date of Patent: * Jul. 24, 1990

[54] PROCESS FOR THE PRODUCTION OF THIOCARBOHYDRAZIDE

[75] Inventors: Dennis E. Jackman, Prairie Village, Kans.; Gary W. Combs, Blue Springs, Mo.; Dietmar B. Westphal, Remscheid, Fed. Rep. of Germany

[73] Assignee: Mobay Corporation, Pittsburgh, Pa.

[ * ] Notice: The portion of the term of this patent subsequent to Jul. 10, 2007 has been disclaimed.

[21] Appl. No.: 324,836

[22] Filed: Mar. 17, 1989

[51] Int. Cl.$^5$ ............................................. C07C 337/06
[52] U.S. Cl. .................................................... 564/18
[58] Field of Search ............................. 564/18; 562/28

[56] References Cited

U.S. PATENT DOCUMENTS 2,726,263  12/1955  Audrieth et al. .................... 260/552
4,172,092  10/1979  Malone ......................... 260/552 SC Primary Examiner—Richard L. Raymond
Assistant Examiner—P. O'Sullivan
Attorney, Agent, or Firm—Joseph C. Gill; Lyndanne M. Whalen

[57] ABSTRACT

Thiocarbohydrazide (TCH) is made by reacting carbon disulfide and hydrazine in the presence of a mercaptan at an elevated temperature. The TCH is removed from the reaction mixture, the mother liquor is further treated to form HDTC which is further reacted to form TCH and the mother liquor is recycled. A major advantage of this process is the recyclability of the mother liquor without reduction in TCH yield.

8 Claims, 2 Drawing Sheets

PROCESS FOR THE PRODUCTION OF THIOCARBOHYDRAZIDE

BACKGROUND OF THE INVENTION

The present invention relates to an improved process for the production of thiocarbohydrazide (TCH).

Several processes for the manufacture of thiocarbohydrazide (TCH) are known. TCH may be obtained during the hydrazinolysis of thiophosgene in an ether or water reaction medium in moderate yields. It is also known to manufacture TCH by hydrazinolysis of diethylxanthate.

It is also known to prepare thiocarbohydrazide through conversion of dialkyltrithiocarbonates with hydrazine. Cyclic trithiocarbonate may also be used for this synthesis.

The most common synthesis of thiocarbohydrazide is, however, the conversion of carbon disulfide with hydrazine. Hydrazinium-dithiocarbazinate (HDTC) forms according to equation (1):

$$CS_2 + 2H_2NNH_2 \rightarrow H_2NNHCSSH \cdot NH_2NH_2 \quad (1).$$

This compound is then converted to thiocarbohydrazide with evolution of hydrogen sulfide according to equation (2):

$$H_2NNHCSSH \cdot NH_2NH_2 \rightarrow H_2NNHCSNHNH_2 + H_2S \quad (2).$$

Better yields and pure product are obtained when the hot aqueous solution of the hydrazinium-dithiocarbazinate is digested with lead oxide (Stolle, et al., Ber. 41, 1099 (1908)).

The yields of thiocarbohydrazide can also be increased when conducting the decomposition of hydrazinium-dithiocarbazinate in aqueous solution in the presence of hydrazine (U.S. Pat. No. 2,726,263). It has been found that increasing the amount of water present in the hydrazine-containing reaction medium decreases the yield of TCH. The use of a water-free solvent for hydrazine (e.g., methyl, ethyl, or propyl alcohol), however, did not increase the TCH yield. In the process disclosed in U.S. Pat. No. 2,726,263, the hydrazinium-dithiocarbazinate (obtained in the usual way through conversion of carbon disulfide with hydrazine hydrate) is heated in an aqueous hydrazine solution at approximately 95° C. for 1-2 hours under reflux. For each mole of hydrazinium-dithiocarbazinate, 1 to 3 moles of hydrazine are used. In a variation of this known process, carbon disulfide is cooled in an aqueous solution with 3 to 6 times the amount of hydrazine and is then heated. In both processes, the yield can be increased by repeatedly removing the TCH which forms during the course of the conversion from the reaction mixture. However, the yield is only 53.3% of theory.

It is also known to convert the hydrazinium-dithiocarbazinate thermally. Yields of approximately 70% of theory are obtained (Petri, Z. Naturforsch, 16B, 769 (1961)) in the thermal conversion process.

When TCH is produced by pyrolyzing a mixture of carbon disulfide and hydrazine hydrate, side reactions which result in the formation of ammonia and sulfur (and concomitant reduction in TCH yield) occur. These side reactions appear to be further catalyzed by the sulfur formed.

It would therefore be advantageous to develop a process for producing TCH from carbon disulfide and hydrazine in which the side reactions resulting in formation of ammonia and sulfur are suppressed.

SUMMARY OF THE INVENTION

It is an object of the present invention to provide improved process for the production of TCH in high yield.

It is also an object of the present invention to provide a process for producing TCH in which formation of ammonia and sulfur by-products is suppressed.

These and other objects which will be apparent to those skilled in the art are accomplished by reacting carbon disulfide with hydrazine in the presence of a mercaptan at an elevated temperature.

DETAILED DESCRIPTION OF THE INVENTION

Figure 1:
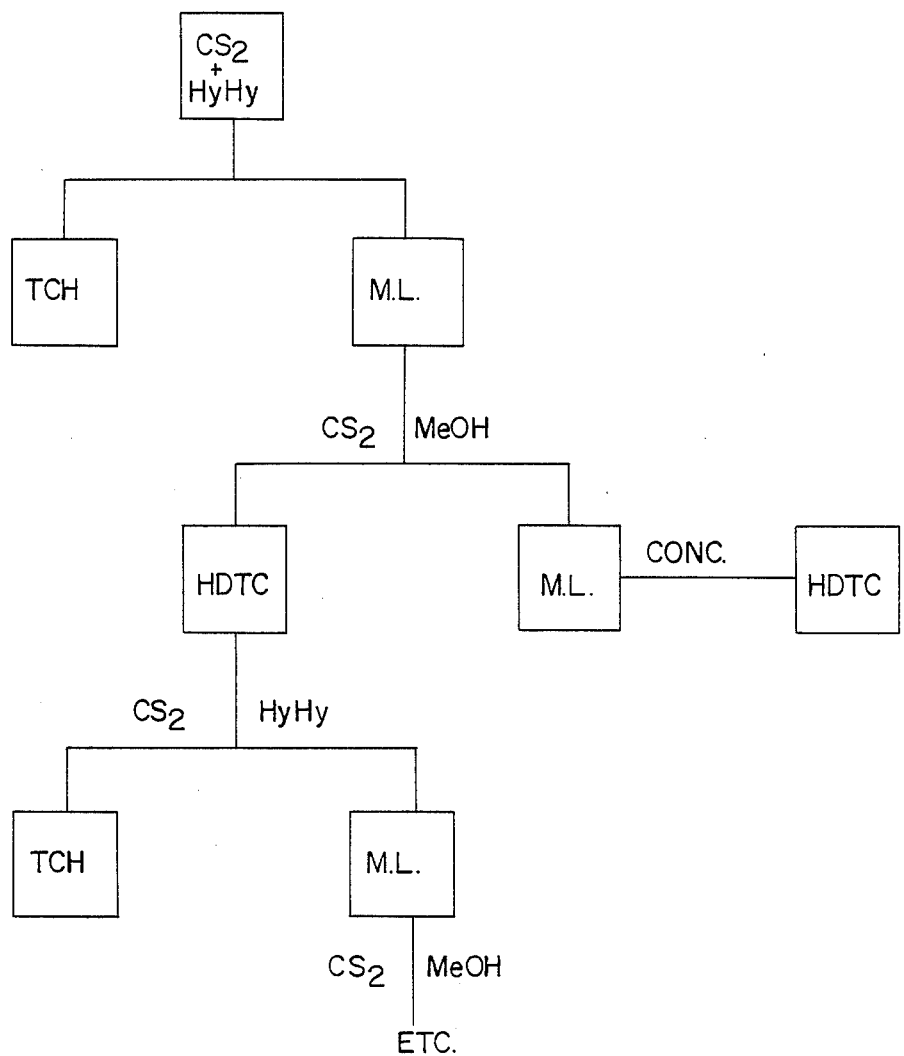
FIG. 1 is a diagram of the process steps for a continuous process within the scope of the present invention.

In the process of the present invention, carbon disulfide and an excess of hydrazine are reacted in the presence of a mercaptan. This reaction which is generally carried out at a temperature of from 20° to 85° C. may be summarized by the following equation:

$$CS_2 + NH_2NH_2 \cdot H_2O + RSH \rightarrow TCH + H_2S.$$

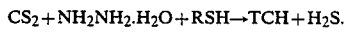

The initial product of carbon disulfide and hydrazine is hydrazinium dithiocarbazinate (HDTC), a water soluble salt formed in nearly quantitative yield at relatively low temperatures (e.g. 20° C.). When the HDTC is heated (e.g. at a temperature of from 50° to 85° C.) in the presence of excess hydrazine, $H_2S$ is given off and TCH forms. The TCH is recovered (e.g. by filtration) and may be washed with water and/or an appropriate alcohol such as methanol. The mother liquid containing unreacted hydrazine is then combined with the TCH-wash and more $CS_2$ to convert the unreacted hydrazine to HDTC.

Where no mercaptan is present in the reaction mixture, the HDTC contains sulfur. When this HDTC containing sulfur is further reacted with hydrazine, TCH and by-products such as

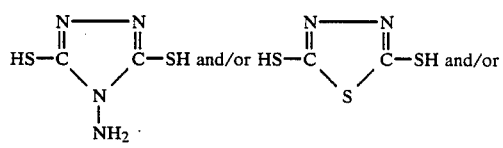

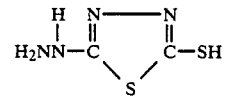

are formed. The yield of TCH may be substantially reduced due to formation of these by-products.

However, the inclusion of a mercaptan in the reaction mixture in accordance with the present invention suppresses the formation of these unwanted by-products. It is believed that the mercaptan intercepts any sulfur as it slowly forms from $H_2S$ and hydrazine. Consequently, the HDTC formed can be used without experiencing the reduction in TCH yield due to by-product formation. Inclusion of a mercaptan in the reaction mixture thus makes it possible to recycle HDTC.

Hydrazine hydrate or an aqueous hydrazine hydrate may be used in the process of the present invention. It is possible to use a commercial grade of hydrazine hydrate, for example, one may even use an 80 to 85% product. Moreover, it is not necessary to use a completely pure hydrazine hydrate. It should be noted that the phrase "water-free hydrazine hydrate" is used herein to identify hydrazine combined with one molecule of water as represented by the formula:

$NH_2NH_2.H_2O$ or $N_2H_5OH$.

The phrase "aqueous hydrazine hydrate" refers to the fact that water has been added to the monohydrate.

In the process for the present invention, one may use either the water-free or the aqueous hydrazine hydrate with good results. The water content of the hydrazine hydrate, however, should preferably not exceed 40% by weight.

The hydrazine hydrate is generally used in the process of the present invention in an amount exceeding that stoichiometrically required to react with the carbon disulfide. An excess of hydrazine of from about 50 to 100% is preferred. Use of a greater excess of hydrazine hydrate is of no particular advantage and is therefore less desirable for economic reasons.

Any mercaptan or thiol (i.e. organic compound resembling an alcohol but having the oxygen of the hydroxyl groups replaced by sulfur) or compound which forms a mercaptan under the reaction conditions may be used in the process of the present invention. Mercaptoethanol, thioglycolic acid, ethane dithiol and other water soluble mercaptans having a high boiling point (i.e. a boiling point greater than the reaction temperature) are particularly preferred. Examples of compounds which form mercaptans under the reaction conditions include ethylene dichloride, 2-chloroethanol and propylene oxide. The mercaptan or mercaptan-forming compound is generally used in a quantity of up to 20 mole %, preferably from 6 to 14 mole % and most preferably from 8 to 12 mole %. When a dithiol is used only half as much (in terms of mole %) is required, because the dithiol provides two SH groups per molecule.

The reaction of carbon disulfide with excess hydrazine takes place most advantageously at a temperature between about 20° C. and 85° C. Reaction temperatures above 85° C. should ordinarily be avoided because under these conditions the reaction proceeds violently and uncontrollably and a very real danger of explosion of the reaction mixture exists. At temperatures of 20° C. and below, the formation of the thiocarbohydrazide does take place but the speed of reaction is relatively slow at these temperatures. The process of the invention is preferably carried out in a temperature range of about 50° C.-80° C. If a short reaction period is to be achieved, the thermal treatment is best carried out at a temperature of about 72° C. to 78° C.

The process of the present invention is particularly advantageous in that it may be carried out on a continuous basis. The mother liquor remaining after the TCH has been removed may be recycled a number of times because deleterious material is not present in any significant amount and the yield of TCH is generally at least 85% of theoretical and is often better than 90%. In fact, the more often the mother liquor is recycled, the higher the yields. TCH yields of from 93-97% can be expected where the mother liquor has been recycled nine times or more.

In one embodiment of a continuous process (as illustrated in FIG. 1), the $CS_2$ and excess hydrazine hydrate are reacted in the presence of a mercaptan to form TCH. The TCH is removed, more $CS_2$ and an organic material in which HDTC is insoluble (such as methanol) are added to the remaining mother liquor. HDTC forms and precipitates at temperatures of from +20° C. to −20° C., preferably about −10° C. over a period of from 0.5 to 2 hrs. The HDTC is recovered (e.g. by filtration) and then added to hydrazine. Carbon disulfide is added to this HDTC and hydrazine mixture and the resultant mixture is heated to a temperature of from 70° to 85° C., preferably 75° to 80° C. for a period of from 16 to 40 hrs, preferably 24 hrs to form a TCH-containing mixture. The TCH is removed to leave a mother liquor which is then treated in the same manner as has already been described (i.e. by adding carbon disulfide, an organic material in which HDTC is insoluble, etc.). The relative quantities of reactants present during any stage of this continuous process and the temperatures employed are the same as described above.

Having thus described our invention, the following examples are given to illustrate its application and effectiveness.

EXAMPLES

Example 1

300 g of hydrazine hydrate and 15 g of mercaptoethanol were charged to a reaction vessel maintained at a temperature of 15° C. 152.2 g of carbon disulfide at 15° C. were then added to the vessel over a period of about two hours. The mixture in the vessel was stirred for 30 minutes and then heated to 70° C. for 16 hours. The resultant slurry was cooled to 30° C. and the solid TCH present was filtered off, washed with a small amount of water and dried. TCH was obtained in a yield of 92% of theoretical (based on $CS_2$).

The mother liquid remaining after TCH removal was recharged to the reaction vessel. 76 g of carbon disulfide at 15° C. were added over a 30 minute period and the mixture was stirred for 30 minutes. The contents of the vessel were then heated to 70° C. A Vigreux column was attached to the vessel to strip off 50 cc of water under vacuum and reduce the volume of the contents of the reactor. When stripping had been completed, 30 g of sodium hydroxide pellets were charged to the reactor. The contents of the reactor were maintained at 70° C. for a total of 16 hours and then cooled to 30° C. The resultant slurry was filtered to recover the solid TCH which was then washed with a small amount of water and dried. TCH was produced in a yield of 79.6% (based on $CS_2$). The overall yield of TCH based on hydrazine used was 87.9%.

Example 2

300.36 g of hydrazine hydrate and 31.25 g of mercaptoethanol at 0°-15° C. were charged to a reaction vessel and then slowly stirred. 152.26 g of carbon disulfide were then slowly added (with stirring) over a thirty minute period while maintaining the contents of the vessel at 20° C. The mixture turned yellow.

The yellow mixture was heated for 12 hours at approximately 70° C. The mixture was filtered to remove the TCH present. These crystals were washed with methanol, ice water and methanol again. The mother liquor and wash materials were charged to the reactor and cooled to 0°-15° C. 1 mole of carbon disulfide was slowly added. H$_2$S was emitted. 192 g of HDTC were recovered and 178.6 g of TCH were recovered.

Example 3

To 6 moles hydrazine hydrate (300.36 g) and 25 g mercaptoethanol were added 2 moles carbon disulfide dropwise while the mixture was stirred and kept at 15°-25° C. by cooling with ice. When the addition was complete, the mixture was stirred for ½ hour at room temperature then heated and stirred at 70° C. for 20 hours. The H$_2$S off-gas was trapped in dilute sodium hydroxide. The reaction mixture was filtered at about 50° C. and the TCH washed with 500 ml of methanol. The combined wash and mother liquor were returned to the flask and 1.06 mole of carbon disulfide was added while the temperature was kept at 15°-20° C. with ice cooling. The solution was stirred for 1 hour at 25° C., then ½ hour at −10° C. and filtered. The recovered HDTC was recycled by placing it in 4 moles hydrazine hydrate and 25 g of mercaptoethanol and adding 1 mole of CS$_2$ dropwise and then heating at 70° C. for 20 hours as described above. TCH yield was about 189 g (89%) on the first reaction. Recycles produced 199-205 g (94-97%). After 1 reaction and 9 recycles, a 95.7% yield TCH based on hydrazine and recovered HDTC was obtained. More TCH could have been obtained by evaporation of the mother liquor.

Example 4

Hydrazine hydrate, mercaptoethanol (ME) and carbon disulfide were reacted at 70° C. for 20 hours to form TCH and a mother liquor containing HDTC which was recycled a total of 9 times by the same procedure that was used in Example 3. The composition of the recycle charge and the yields obtained are given in the following Table 1.

TABLE 1

| Initial Charge: | Recovery Charge: |
|---|---|
| 6 Moles hydrazine hydrate (HyHy) | TCH mother liquor |
| 2 Moles CS$_2$ | 500 ml MeOH |
| 30 g mercaptoethanol | 1.06 Moles CS$_2$ |

| Recycle Charge: | |
|---|---|
| rec. HDTC | Reaction time: 20 hrs |
| 4 Moles hydrazine hydrate | Reaction temp: 70° C. |
| 1 Mole CS$_2$ | HDTC Recovery Temp: −10° C. |
| 30 g mercaptoethanol | |

| Moles HyHy | Recycle | gm TCH | A.I. | gm TCH |
|---|---|---|---|---|
| 6 | 0 | 189 | 100 | 189 |
| 4 | 1 | 199 | 98 | 195 |
| 4 | 2 | 199 | 98 | 194 |
| 4 | 3 | 197 | 99 | 195 |
| 4 | 4 | 202 | 99 | 200 |
| 4 | 5 | 202 | 99 | 200 |
| 4 | 6 | 203 | 99 | 201 |
| 4 | 7 | 207 | 100 | 207 |
| 4 | 8 | 203 | 99 | 201 |
| 4 | 9 | 205 | 97 | 199 |
| Total | 42 | | 2015 | 98.8 ave | 1990 g |

HDTC recovered = 188 g = 1.34 moles
TCH produced = 1990 g = 18.76 moles
TCH yield = 92.8%
HDTC yield = 134.3%
Hydrazine accountability as TCH + HDTC = 95.7%

Example 5

Figure 2:
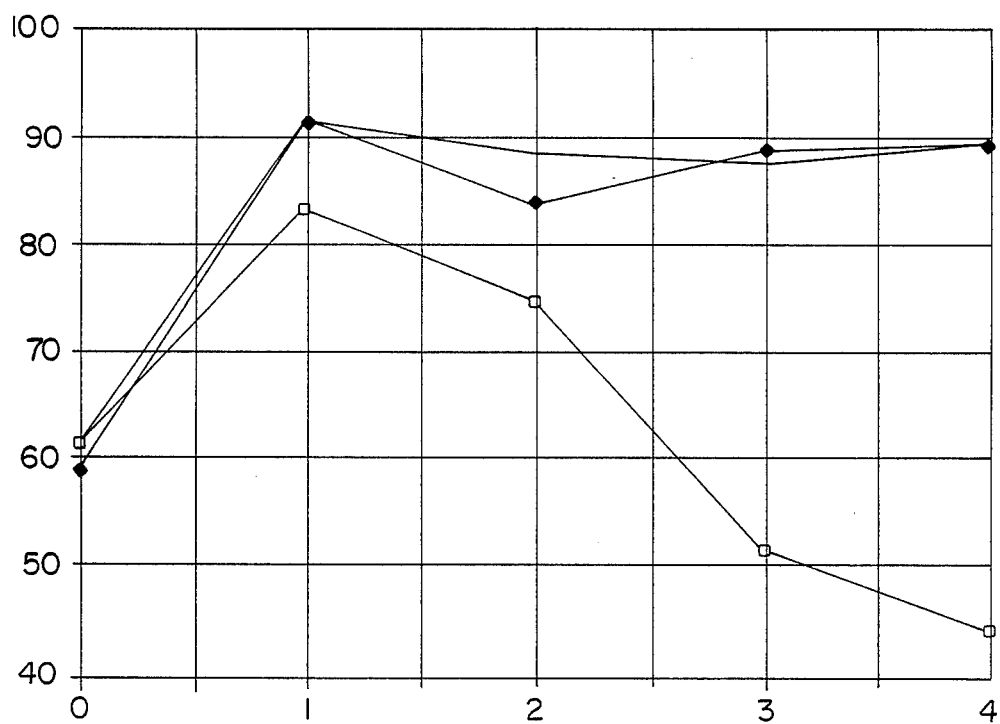
FIG. 2 is a graphic illustration of the effect addition of mercaptoethanol has upon the yield of TCH.

The effect of adding mercaptoethanol in varying amounts was studied for recycle HDTC. Each batch was started with fresh HDTC, excess hydrazine (1 mole/mole HDTC), water (2 moles/mole HDTC) and varying amounts of mercaptoethanol. Each batch was pyrolyzed at 66° C. for 12 hours, cooled and filtered. CS$_2$ was then added to the hydrazine-containing mother liquor. HDTC was filtered out, the recovered HDTC was mixed with fresh HDTC and pyrolyzed as in the first batch. The results are graphically illustrated in FIG 2.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of TCH comprising reacting hydrazine and carbon disulfide in the presence of a mercaptan or a mercaptan-forming compound at a temperature of from 20° to 85° C.

2. The process of claim 1 in which mercaptoethanol is the mercaptan employed.

3. The process of claim 1 in which the TCH formed is separated from the reaction mixture and the remaining portion of the mixture is recycled.

4. The process of claim 1 in which hydrazine hydrate is employed in a 50% excess.

5. The process of claim 1 in which the mercaptan used is thioglycolic acid.

6. A process for the production of TCH comprising:
   (a) reacting excess hydrazine and carbon disulfide in the presence of a mercaptan at a temperature of from 20° to 85° C. to form TCH,
   (b) recovering the TCH formed in (a) and adding carbon disulfide and an organic material in which HDTC is insoluble to the portion of the mixture formed in (a) remaining after the TCH has been recovered,
   (c) recovering HDTC from the mixture of (b),
   (d) combining the HDTC recovered in (c) with hydrazine and carbon disulfide,
   (e) heating the mixture of (d) to a temperature of from 20° to 85° C. to form TCH, and
   (f) recovering the TCH formed in (e) and treating the remaining portion of the mixture in the same manner as the comparable mixture obtained in (b).

7. The process of claim 6 in which the mercaptan is mercaptanethanol.

8. The process of claim 7 in which the organic material in which HDTC is insoluble is methanol.

* * * * *